United States Patent [19]

Barasch

[11] Patent Number: 4,928,824
[45] Date of Patent: May 29, 1990

[54] HYPODERMIC NEEDLE SHEATH PROTECTION SHIELD APPARATUS

[76] Inventor: Stephen T. Barasch, 2335 Edgewater La., Largo, Fla. 34644

[21] Appl. No.: 96,732

[22] Filed: Sep. 15, 1987

[51] Int. Cl.$^5$ ............................................. A61M 5/00
[52] U.S. Cl. ................................... 206/365; 604/263; 604/192
[58] Field of Search ................. 206/365; 604/263, 192

[56] References Cited

U.S. PATENT DOCUMENTS

| 3,342,319 | 9/1967 | Faulseit | 206/365 |
|---|---|---|---|
| 3,677,247 | 7/1987 | Brown | 206/365 X |
| 4,113,090 | 9/1978 | Carstens | 206/365 |
| 4,116,196 | 9/1978 | Kaplan et al. | 604/192 |
| 4,287,988 | 9/1981 | House | 206/365 |
| 4,485,918 | 12/1984 | Mayer | 206/366 |
| 4,559,042 | 12/1985 | Votel | 604/192 |
| 4,573,975 | 3/1986 | Frist et al. | 604/263 X |
| 4,576,281 | 3/1986 | Kirksey | 206/370 |
| 4,610,667 | 9/1986 | Pedicano et al. | 604/263 X |
| 4,629,453 | 12/1986 | Cooper | 604/192 |
| 4,636,201 | 1/1987 | Ambrose et al. | 604/192 |
| 4,643,722 | 2/1987 | Smith, Jr. | 604/192 |
| 4,654,034 | 3/1987 | Masters et al. | 604/192 |
| 4,664,259 | 5/1987 | Landis | 206/365 |

FOREIGN PATENT DOCUMENTS

| 717777 | 9/1965 | Canada | 206/365 |
|---|---|---|---|
| 831756 | 2/1952 | Fed. Rep. of Germany | 206/365 |
| 1815790 | 3/1970 | Fed. Rep. of Germany | 206/365 |
| 92437 | 9/1968 | France | 206/365 |
| 2586566 | 3/1987 | France | 604/192 |
| 828050 | 2/1960 | United Kingdom | 604/263 |

Primary Examiner—William Price

[57] ABSTRACT

A sheath for a hypodermic needle or other sharp instrument which is adapted with an apparatus to protect the hand of a person attempting to insert the hypodermic needle or sharp instrument into the sheath and the protection apparatus, wherein the protection apparatus generally comprises a radial shield or a shroud extending out from the sheath a distance which is adequate to block, deflect, or separate a stray hypodermic needle which inadvertantly misses the entry port of the sheath from a person's sheath-holding hand.

2 Claims, 8 Drawing Sheets

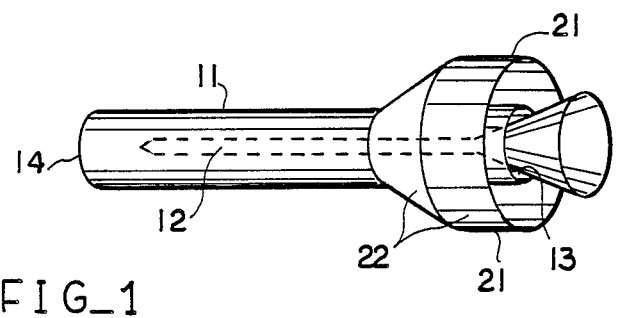
FIG_1
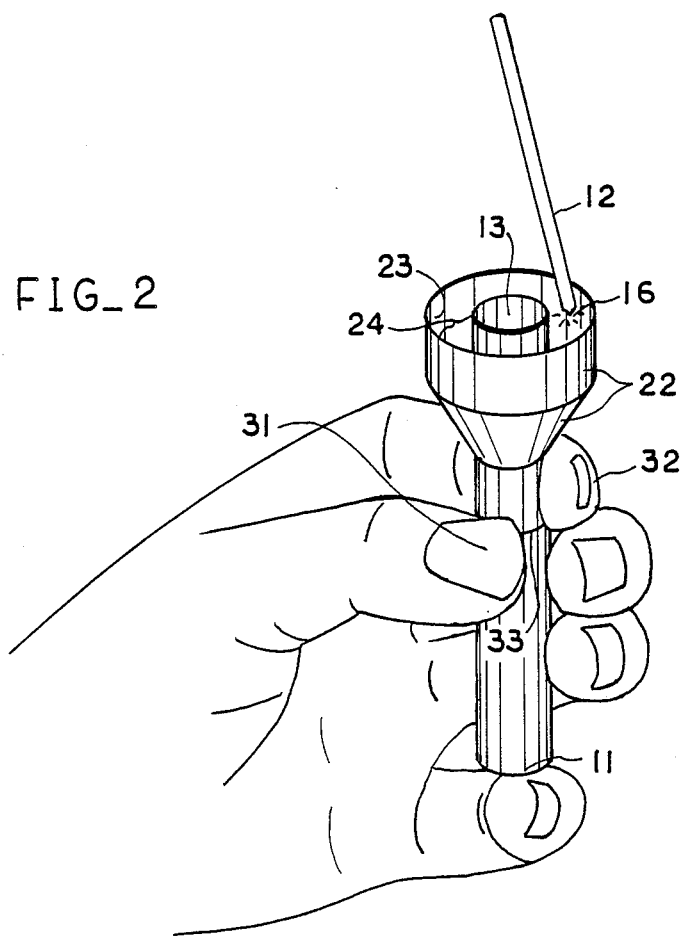
FIG_2

FIG_3
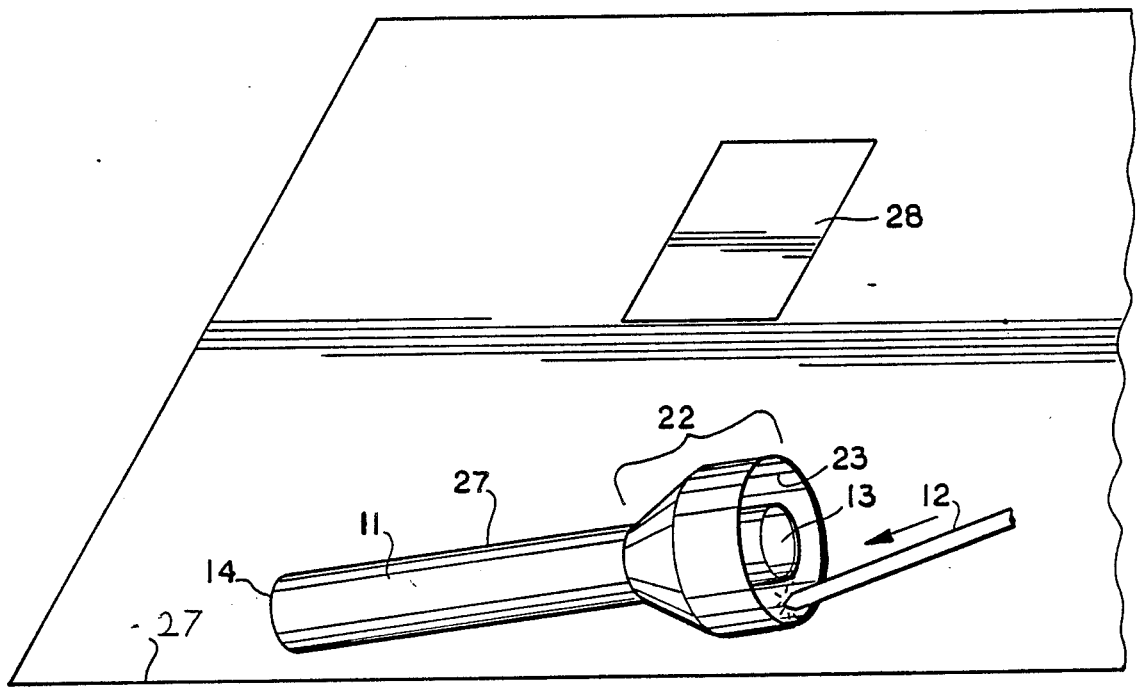

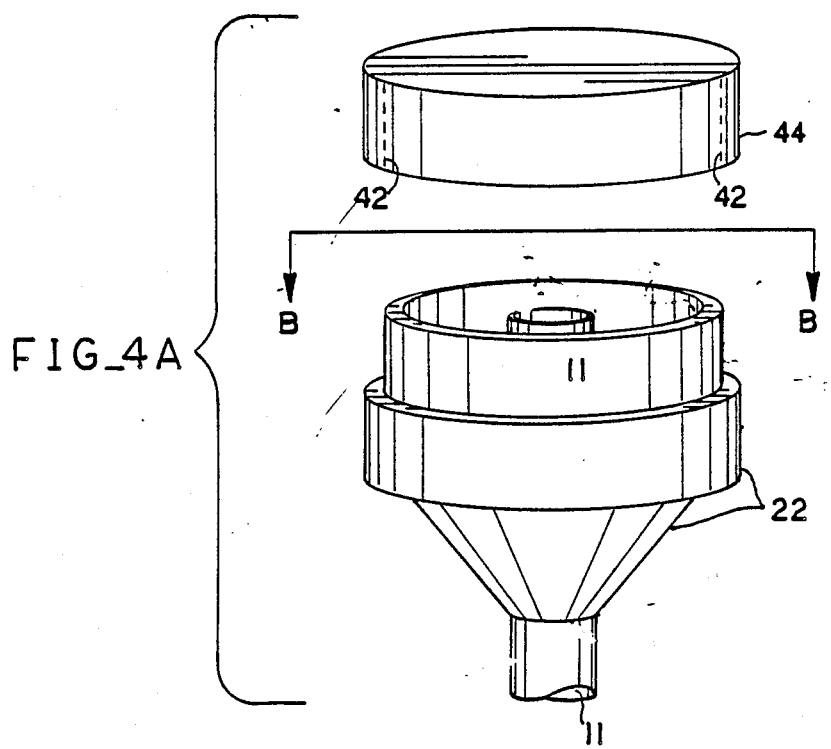
FIG_4A
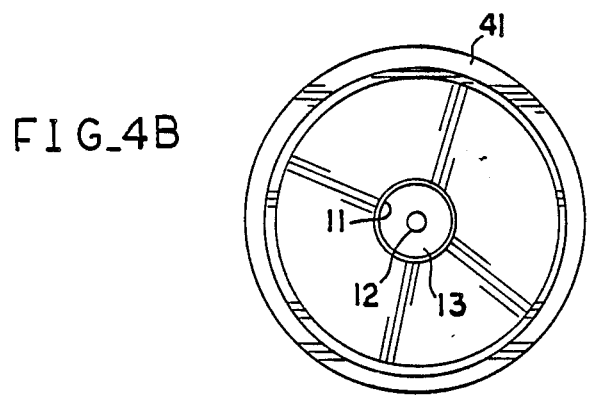
FIG_4B

FIG_5A
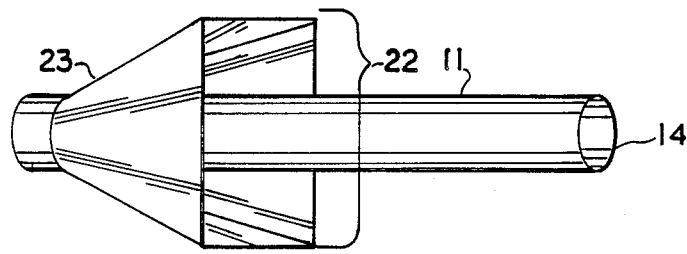
FIG_5B
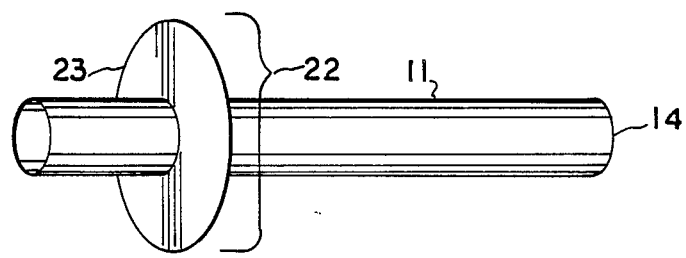
FIG_5C
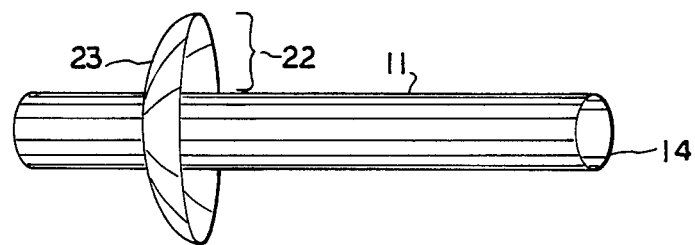
FIG_5D
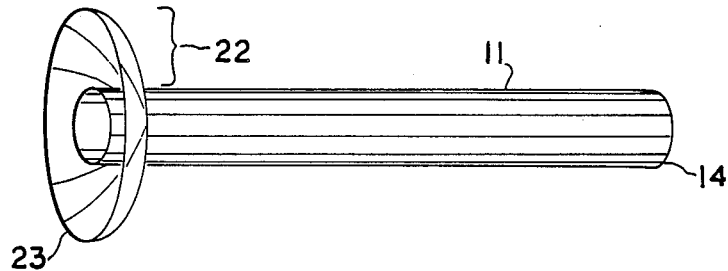

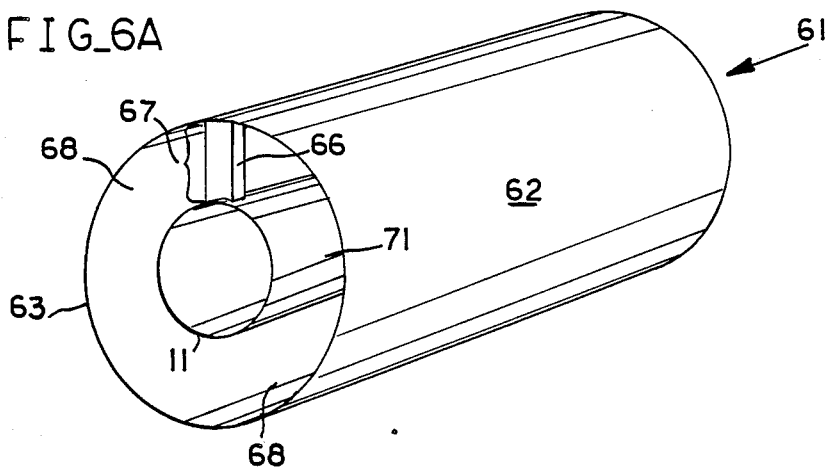
FIG_6A
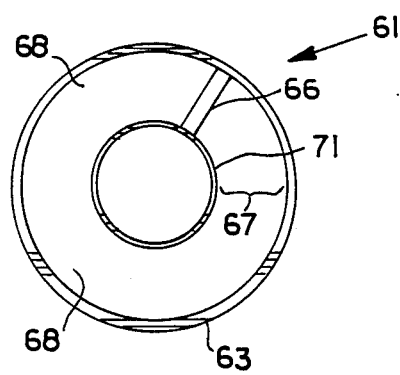
FIG_6B
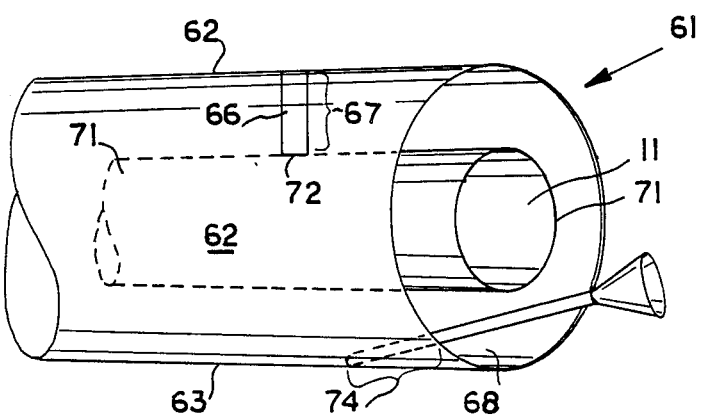
FIG_7

FIG_8
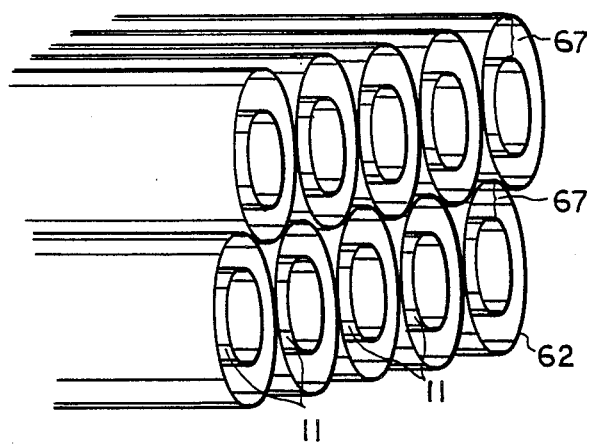
FIG_9
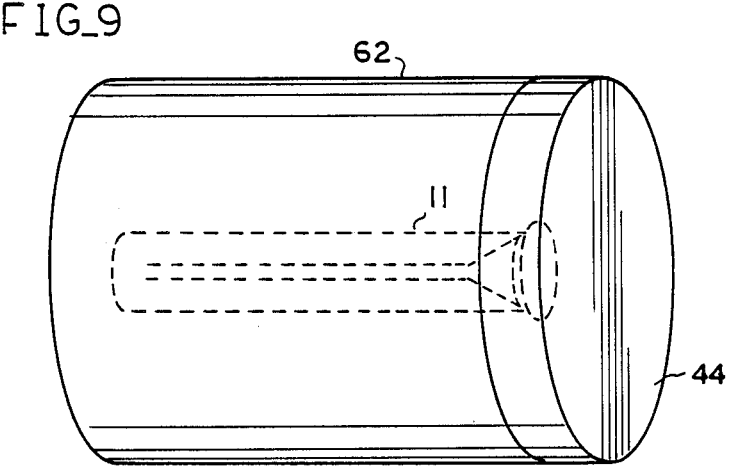

FIG_10A
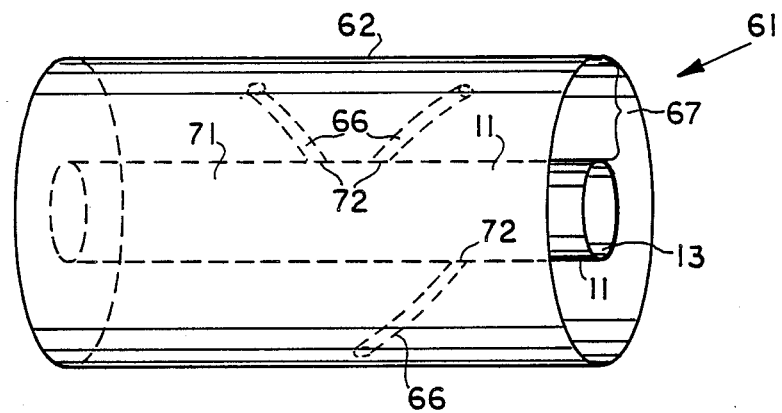
FIG_10B
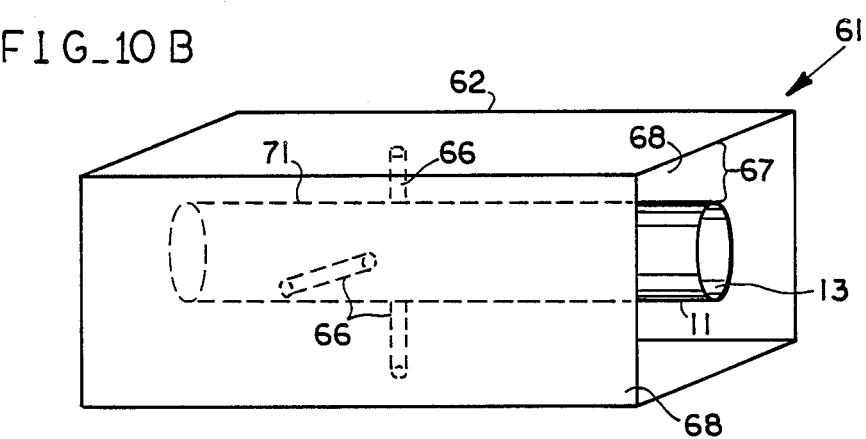

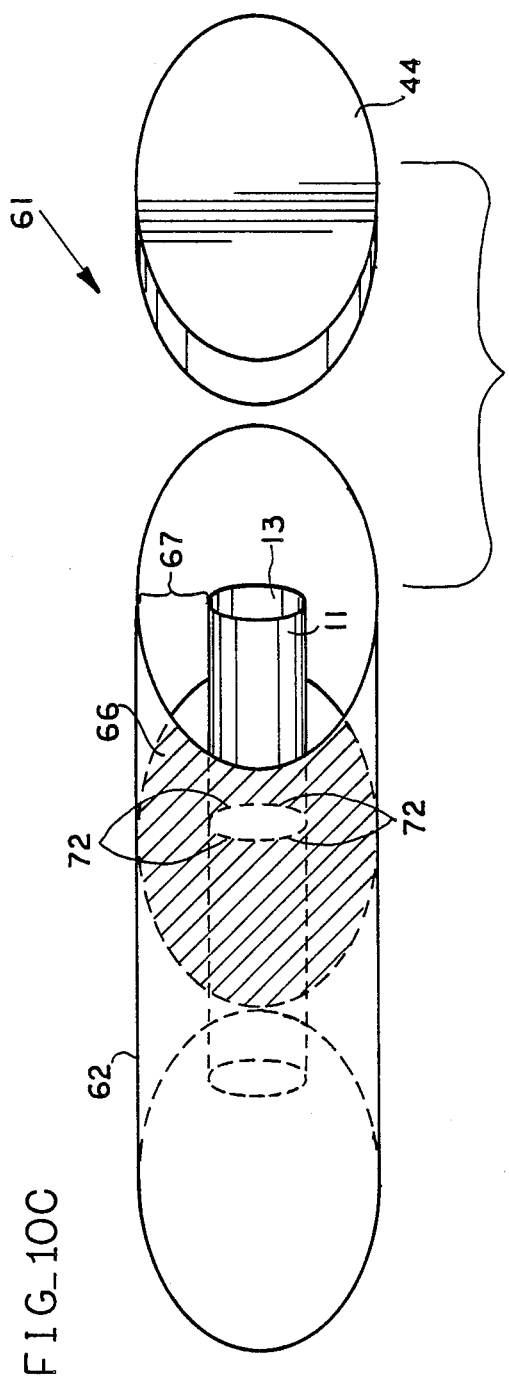
FIG_10C

HYPODERMIC NEEDLE SHEATH PROTECTION SHIELD APPARATUS

BACKGROUND OF THE INVENTION

The invention relates to devices useful in the packaging, storage, and transport of medical hypodermic needles.

It has commonly become the case that hypodermic needles, in modern medical practice, are limited to a single use prior to their disposal. This is because of the increased concerns posed by communicable diseases, many of which, like AIDS, are readily passed along by body fluid exchange, via inadvertent needle puncture, coupled with the relative low cost of the hypodermic needle itself. Indeed, it is frequently made hospital policy that hypodermic needles not be reused and, in order to prevent the risk of even accidental puncture, that they not be bent or even recapped.

Often, however, there are situations in which the reuse, or recapping, of a hypodermic needle may be advantageous. An anaestheseologist, during a prolonged operation, frequently needs to have a number of various medications available to him in order to respond to a patient's operative condition. The anaestheseologist will be required to alternately select between the medications and will need to have each immediately available. Because the medications can be injected into an intravenous system rather than through the patient's skin, the risks associated with the previously described communicable disease problem are not present.

It is widely accepted within the surgical art that the ambient atomosphere present within an "open-patient" environment contains germs and bacteria impurities which are inherently present. The longer an open patient or surgical tool, such as a hypodermic needle, is exposed to such ambient atmosphere, the greater the risk of infection to the patient. It would then, be to the benefit of an anaestheseologist working in that environment to have the ability to have a measured amount of given medications immediately available and the ability to safely and cleanly use, resheath and cover in a manner providing minimal exposure to the ambient atmosphere, and then reuse a hypodermic needle affixed to a syringe containing such medication would be most beneficial.

While a needle or surgical device exposed only to the air for some reasonable time may still be considered "clean" for further use, any such instrument coming into direct contact with another person or object is immediately rendered non-sterile. Therefore, it is necessary to ensure that, in any situation in which a needle is to be resheathed, that both the needle and any part of the sheath with which the needle may make contact are isolated from contact with any other object.

The ability to safely resheath or recap a hypodermic needle to be disposed after only one use may be desirable. On the other hand, even if it is desirable to dispose of a needle after only a single use, recapping of the needle be of benefit in this instance as well. Since there are risks associated with bending, or otherwise marking a used hypodermic needle, such a hypodermic needle should be immediately transported to a safe disposal utensil. While being handled and in transport, particularly in a crowded and busy patient location, the risks of inadvertently puncturing oneself or another is significant. The ability to safely recap the hypodermic needle immediately after use and before transport or disposal, then, would also be of benefit.

A number of inventions teach various methods of packaging, storing, or disposing of hypodermic needles. Various devices, such as Mayer (U.S. Pat. No. 4,485,918) and Smith (U.S. Pat. No. 4,643,722) teach hypodermic needle storage, transport, and disposal devices which afford some measure of protection to the individual handling the needle at that time. In particular, each of these provide a funnel-like for channeling the tip of the hypodermic needle into its sheath. However, needles disposed of in this manner cannot be rendered suitable for reuse, nor do the inventions protect a person during transport of the needle to the disposal area.

Carstens (U.S. Pat. No. 4,113,090) points out the advantages of having a "hard" package for the packaging of hypodermic needles which additionally permits accessibility via a cap or other opening means not requiring the destruction of the package. This permits storage sterilization as well as personal protection from inadvertent puncture. After use of the hypodermic needle, even when disposal is desired, this permits safer disposal of the hypodermic needle by providing a "hard" and resealed disposal vessel.

What is needed in the art is an apparatus for promoting both safe reinsertion of the hypodermic needle into its sheath and safe transport or disposal.

SUMMARY OF THE INVENTION

The present invention comprises a hypodermic needle sheath which is adapted with a simple shielding apparatus for the protection of the sheath-holding hand of a person attempting to insert the hypodermic needle into its sheath. Variations of the apparatus include means for capping the sheath so as to enclose the hypodermic needle within the sheath. The shield may also be adapted so as to prevent any portion of the sheath, when laid down, from contacting any other object in a place where the sheath and the needle might inadvertantly make contact.

It is an object of the invention to provide a means for permitting safer insertion of a hypodermic needle within its sheath.

It is a further object of the invention to maintain cleanliness of the reinserted needle to permit re-use of the needle.

Other features and advantages of the present invention will be apparent from the following description in which the preferred embodiments have been set forth in conjunction with the accompanying drawings.

DETAILED DESCRIPTION OF THE PREFERRED EMBODIMENTS

In describing the preferred and an alternate embodiment, reference will be made to the accompanying FIGS. 1 through 10. Broken lines indicate portions of the apparatus which are enclosed within another surface.

FIGS. 1 through 5D generally depict an embodiment of the invention which protects the person's hand from the needle by blocking it with some form of a shield about the sheath. Alternative designs incorporating this embodiment are also depicted.

FIGS. 6 through 10a depict elements and features of an embodiment of the invention which protect a person's hand by isolating the grasping area of the sheath with some form of shroud. Again, alternative designs incorporating the elements of this embodiment are depicted.

Making reference now to FIG. 1, the preferred embodiment of the invention is described. A sheath (11) for a hypodermic needle (12) is adapted with a protection apparatus (21). The protection apparatus (21) in the preferred embodiment is comprised of a radial shield (22) situated near the open end (13) of the sheath (11). The radial shield (22) as depicted herein is tapered towards the closed end (14) of the sheath (11).

Making reference now to FIG. 2, the use of the preferred embodiment is described. By gripping the sheath (11) between the thumb (31) and forefinger (32) at a point (33) opposite the open end (13) from the radial shield (22) of one hand, a person can use the other hand to insert the point (16) of a hypodermic needle (12) into the sheath (11).

The protecting surface (23) of the radial shield (22) protects the thumb (31) and forefinger (32) from inadvertent puncture by a hypodermic needle's point (16) which misses the open end (13) of the sheath (11) within a range (23) which would be equal to the maximum reasonable distance by which a person may inadvertantly miss the open end (13) of the sheath (11) by blocking the hypodermic needle's point (16) before it could strike the thumb (31) or forefinger (32). The nurse or physician may then reattempt insertion of the hypodermic needle (12) into the sheath (11).

FIG. 3 depicts how the invention operates to protect the needle (12) from inadvertent contact with any unclean surface or object during a sheathing.

By positioning the radial shield (22) at a point along the sheath (11) which is nearer the open end (13) then the closed end (14), the sheath (11) will then, when empty and laid down, settle such that the open end (13) is elevated from the supporting surface (26) and portions of the shield (generally, 23) which may make contact with a stray needle (12) directed into but missing the open end (13) of the sheath (11) are also protected from inadvertent contact with potentially contaminating objects or surfaces (27) and (28).

In the embodiment of the invention, as depicted in FIG. 4A and FIG. 4B, the radial shield (22) can be adapted with a surface (41) permitting the sheath to hold a cap (44) over the open end (13) of the sheath (11) and hypodermic needle (12). This permits the hypodermic needle (12) to be sealed off from the surrounding atmosphere in circumstances where the guarantee of sterility is required such as in original shipping or pre-use storage. In this adaptation, the needle (12) would be placed within the sheath (11) and capped at the place of manufacture. A capped sheath (not depicted) could be removed from its factory packaging without loss of sterility until the cap (44) were removed.

FIGS. 5A through 5D generally depicts various alternative forms of the invention. It should generally be noted that, in each form, the protecting surface (23) of the shield (22) is nearer the open end (13) of the sheath (11). Within that general specification a variety of shapes and sizes of radial shields (22) is possible, although it is recognized that some forms may permit exposure of the protecting surface (23) of the radial shield (22) to unclean areas and would be useful only for protection of fingers.

In another embodiment of the invention, as depicted in FIGS. 6A, 6B and 7, a different protection apparatus (61) essentially comprises a shroud (generally 62) about the sheath (11). The shroud (generally 62) may be fixed to the sheath's external surface (71) at any desired point (72) by a joining member (66). The shroud (generally 62) is generally parallel to the sheath (11) and separates the sheath's external surface (71) by some distance (67) from the shroud's external surface (63).

The joining member (66) may, but need not, resemble the radial shield (22) of the previously described embodiment of the invention. For instance, FIG. 6A depicts a slightly oblique cross-sectional view of a sheath (11) from the open end. The sheath (11) is joined to the shroud (generally 62) by a joining member (66) which comprises a single rod-like piece.

FIG. 7 depicts this embodiment from a side view and also depicts a needle which has strayed beyond the open end of the sheath (11). The stray needle of this embodiment is more likely to avoid contact with any other object as the shroud (generally 62) shields the sheath-holding fingers and thumb by separating them from the needle by its separating distance (67) rather than blocking the needle with a protecting surface.

As the shroud (generally 62) may be joined with the sheath at any point along its length, the needle may be plunged into the shroud-enclosed space (68) for a considerable distance (74) along its length before approaching any object, thus decreasing the probability of needle contact with any undesired surfaces. The joining member (66) must still be of sufficient strength and rigidity to withstand the impact of the stray needle against either the sheath or the joining member (66) as the stray needle may hit the edge of the open end of the sheath. This would put nearly as much pressure on the joining member (66) as a direct hit upon the joining member (66) itself.

This embodiment also has the advantages of easier storage and handling. Since the shroud (generally 62) can be designed to give the apparatus a more regular profile, a quantity of such devices can be permitted to be neatly stacked or laid out as is depicted in FIG. 8. Because all points on the shroud's external surface (63) are separated from the sheath's open end (13) by a safe distance (67), the apparatus of this embodiment can be gasped at any point along the shroud's external surface (63) with the same relative safety. For the same reason however, this embodiment would likely be somewhat more bulky than the other embodiment.

FIG. 9 depicts this embodiment which is further adapted with a cap. It should be noted, however, that only a shroud (generally 62) which can either be capped at both ends or which also comprises a member (which could be the joining member (66)) which radially closes off the protecting space from the ambient air at the uncapped end would benefit from a cap adaptation.

FIGS. 10A, 10B and 10C depicts how this embodiment may also be made in a variety of designs incorporating its general characteristics. Both the shape of the shroud (generally 62) and the style of joining members (66) may be varied.

Further modification and variation can be made to the disclosed embodiments without departing from the subject and spirit of the invention as defined in the following claims. Such modifications and variations, as included within the scope of these claims, are meant to be considered part of the invention as described.

What is claimed is:

1. An apparatus for the sheathing of a hypodermic needle which is adapted to protect a person's sheath-holding hand during sheathing, said apparatus comprising;

a sheath for a hypodermic needle;

said sheath being fastened at some point to at least one joining member, said joining member being further fastened to a shrouding member such that such fastened joining member is of adequate strength and rigidity to remain fastened under the pressure caused by the impact of a stray needle during a sheathing operation to either said joining member, said sheath, or said shrouding member;

said shrouding member further comprising an external surface which is generally parallel with the external surface of said sheath and surrounds said sheath along some part of the length of said sheath;

said shrouding member external surface being, at all points, some distance from the nearest point on said sheath external surface.

2. The invention described in claim 1 in which said shrouding member is adapted to be capped, said apparatus further comprising;

a closing member, said closing member making a full radial connection between said sheath and said shrouding member so as to close off atmospheric communication between the shrouding member-enclosed space at the end of said shrouding member which is nearest the open end of said sheath and the ambient air of the surrounding space;

a capping apparatus, said capping apparatus further comprising;

a hollow cap member having a diameter equal to the diameter of said said shrouding member end;

a said hollow cap member being of length which is at least equal to the distance from the outer perimeter of said shrouding member end and the open end of said hollow sheath member as extended by a needle housed within;

said hollow cap member having one closed cap end and one open cap end;

said open cap end having a perimeter which is congruent with the edge of said said shrouding member end and further adapted with a means for fastening said cap to said shrouding member end such that said capping apparatus encloses the open end of said hollow sheath member and any needle housed within.

* * * * *